US012697354B2

(12) United States Patent
Yang et al.

(10) Patent No.: US 12,697,354 B2
(45) Date of Patent: Aug. 4, 2026

(54) PHARMACEUTICAL COMPOSITION COMPRISING HYALURONIC ACID AND STEM CELLS FOR TREATING CARTILAGE DAMAGE-ASSOCIATED DISEASE

(71) Applicant: MEDIPOST CO., LTD, Seongnam-si (KR)

(72) Inventors: Yun Sun Yang, Seongnam-si (KR); Wonil Oh, Seongnam-si (KR); Soo Jin Choi, Seongnam-si (KR); Miyoung Lee, Seongnam-si (KR); Jueun Ha, Seongnam-si (KR); Minju Lee, Seongnam-si (KR)

(73) Assignee: MEDIPOST CO., LTD, Seongnam-si (KR)

( * ) Notice: Subject to any disclaimer, the term of this patent is extended or adjusted under 35 U.S.C. 154(b) by 957 days.

(21) Appl. No.: 16/972,373

(22) PCT Filed: Jun. 5, 2019

(86) PCT No.: PCT/KR2019/006816
§ 371 (c)(1),
(2) Date: Dec. 4, 2020

(87) PCT Pub. No.: WO2019/235853
PCT Pub. Date: Dec. 12, 2019

(65) Prior Publication Data
US 2021/0228637 A1     Jul. 29, 2021

Related U.S. Application Data

(60) Provisional application No. 62/680,748, filed on Jun. 5, 2018.

(51) Int. Cl.
| | |
|---|---|
| *A61K 35/28* | (2015.01) |
| *A61K 9/00* | (2006.01) |
| *A61K 31/728* | (2006.01) |
| *A61K 35/51* | (2015.01) |
| *A61P 11/06* | (2006.01) |
| *A61P 19/02* | (2006.01) |
| *A61P 25/28* | (2006.01) |

(52) U.S. Cl.
CPC ............ *A61K 35/28* (2013.01); *A61K 9/0019* (2013.01); *A61K 31/728* (2013.01); *A61K 35/51* (2013.01); *A61P 11/06* (2018.01); *A61P 19/02* (2018.01); *A61P 25/28* (2018.01)

(58) Field of Classification Search
CPC .............................. A61K 31/728; A61K 35/28
See application file for complete search history.

(56) References Cited

U.S. PATENT DOCUMENTS

| | | | | |
|---|---|---|---|---|
| 7,459,307 | B2 * | 12/2008 | Ha | .......... A61K 35/28 |
| | | | | 435/325 |
| 2006/0069064 | A1 | 3/2006 | Khaldoyanidi | |
| 2007/0128155 | A1 | 6/2007 | Seyedin et al. | |
| 2016/0184364 | A1 * | 6/2016 | Gupta | .................. A61K 9/0019 |
| | | | | 424/93.7 |

FOREIGN PATENT DOCUMENTS

| | | |
|---|---|---|
| CN | 104840486 A | 8/2015 |
| KR | 2003-0015160 A | 2/2003 |
| WO | 2017/147649 A1 | 9/2017 |

OTHER PUBLICATIONS

Ha et al. "Cartilage Repair Using Composites of Human Umbilical Cord Blood-Derived Mesenchymal Stem Cells and Hyaluronic Acid Hydrogel in a Minipig Model". Stem Cells Transl Med. Sep. 2015;4(9):1044-51. (Year: 2015).*
Abate et al, "Hyaluronic acid in knee osteooarthritis: preliminary results using a four months administration schedule". International J Rheumatic Diseases, 2017, vol. 20, pp. 199-202. (Year: 2017).*
Migliore et al., "Intra-articular use of hyaluronic acid in the treatment of osteoarthritis". Clin Interv Aging. 2008;3(2):365-9. (Year: 2008).*
Goldberg et al., "The use of mesenchymal stem cells for cartilage repair and regeneration: a systematic review", Journal of Orthopaedic Surgery and Research, Mar. 9, 2017, vol. 12, No. 39, pp. 1-30 (30 pages total).
Jose M. Lamo-Espinosa, et al., "Intra-articular injection of two different doses of autologous bone marrow mesenchymal stem cells versus hyaluronic acid in the treatment of knee osteoarthritis: multicenter randomized controlled clinical trial (phrase I/II)", Journal of Translational Medicine, 2016, pp. 1-10, vol. 14, No. 246.
International Searching Authority, International Search Report for PCT/KR2019/006816 dated Sep. 3, 2019 [PCT/ISA/210].
International Searching Authority, Written Opinion for PCT/KR2019/006816 dated Sep. 3, 2019 [PCT/ISA/237].

(Continued)

*Primary Examiner* — Christopher M Babic
*Assistant Examiner* — Hanan Isam Abuzeineh
(74) *Attorney, Agent, or Firm* — Sughrue Mion, PLLC

(57) ABSTRACT

A pharmaceutical composition containing hyaluronic acid and mesenchymal stem cells and its use in treating cartilage damage-associated diseases are disclosed. Compared to when hyaluronic acid and mesenchymal stem cells are administered as a mixture, administering mesenchymal stem cells after first administering hyaluronic acid may exhibit superior effects in alleviating disease symptoms in joint tissues affected by arthritis and also decrease the load on knees due to body weight. Accordingly, the pharmaceutical composition may be beneficially used in the treatment of cartilage damage-associated diseases.

10 Claims, 4 Drawing Sheets

(56)                    References Cited

OTHER PUBLICATIONS

Peter Succar, et al., "Priming Adipose-Derived Mesenchymal Stem
Cells with Hyaluronan Alters Growth Kinetics and Increases Attach-
ment to Articular Cartilage," Hindawi Publishing Corporation, Stem
Cells International, 2016, vol. 2016, Article ID 9364213, pp. 1-13
(14 pages total).
Korean Office Action issued Jun. 5, 2024 in Application No.
10-2020-7036315.

* cited by examiner

[FIG. 1]
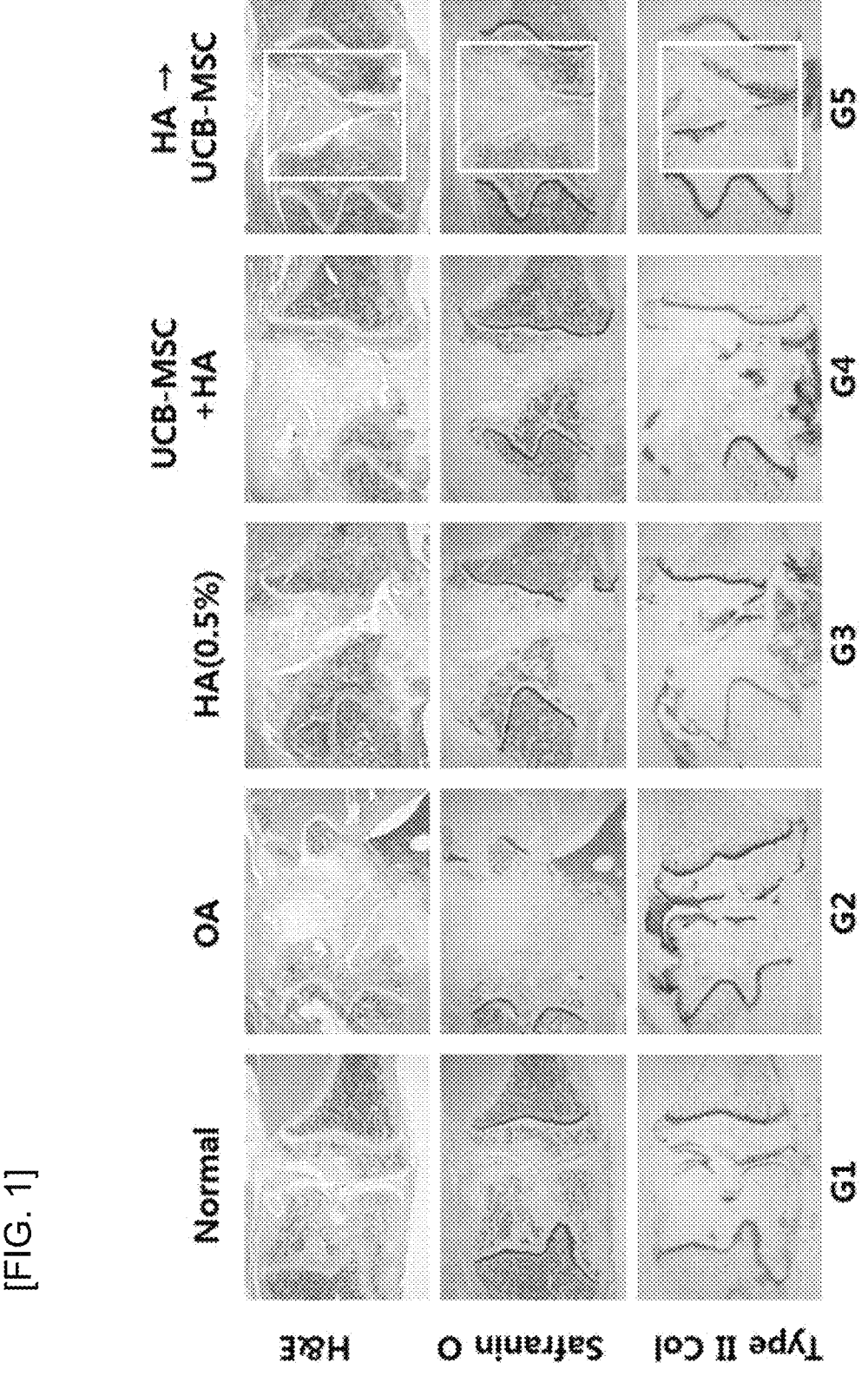

[FIG. 2]
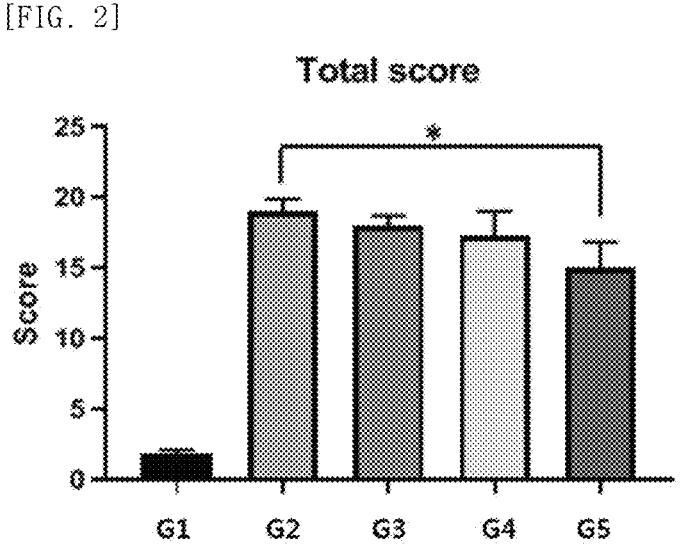
[total score]
G2 vs G3, $p$ value= 0.55
G2 vs G4, $p$ value= 0.31
G2 vs G5, $p$ value= 0.22
[FIG. 3]
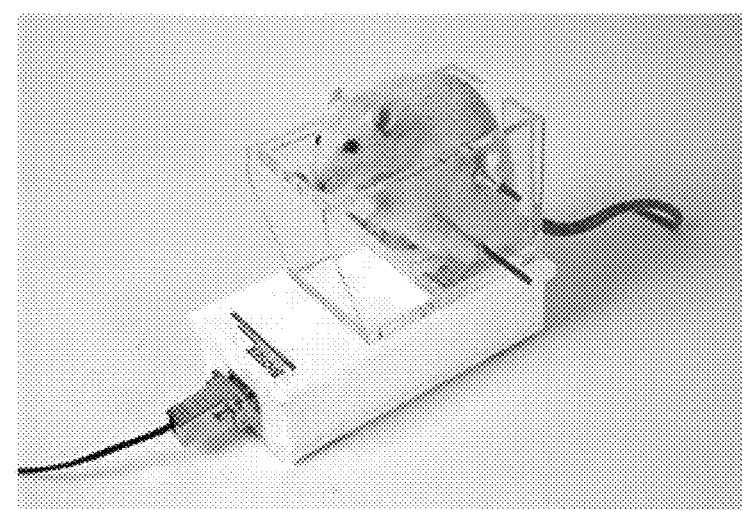

[FIG. 4]
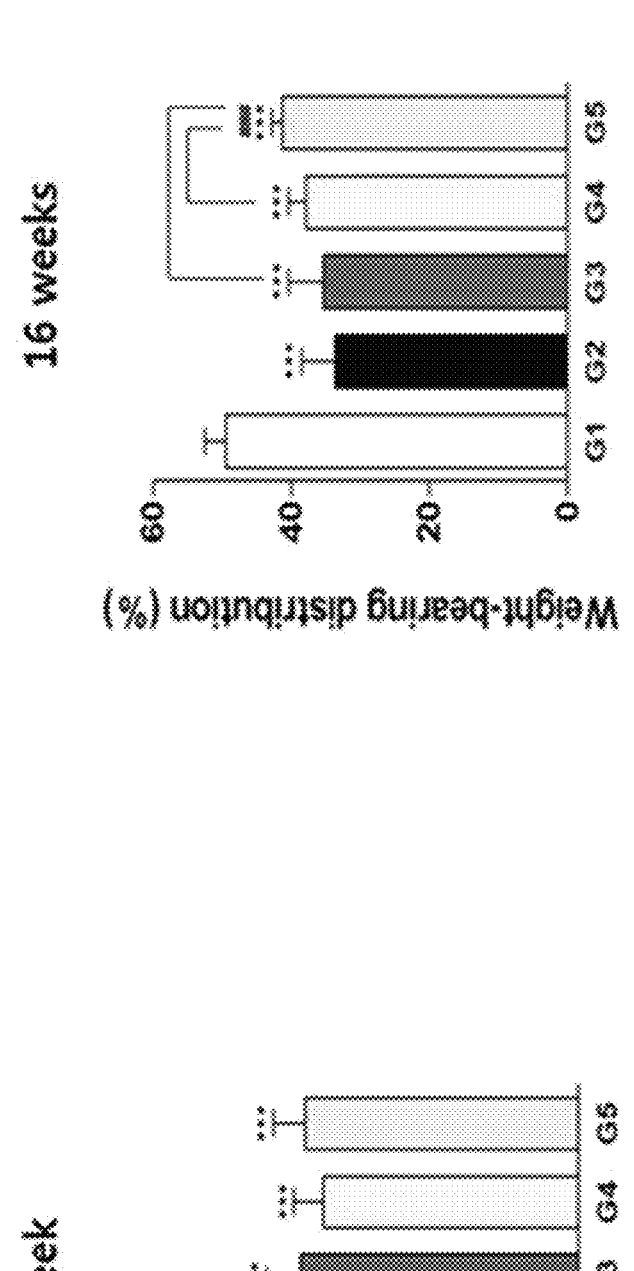
G1: Normal, G2: OA, G3: HA(0.5%), G4: MSC+HA(0.5%), G5: HA(0.5%)→MSC

[FIG. 5]
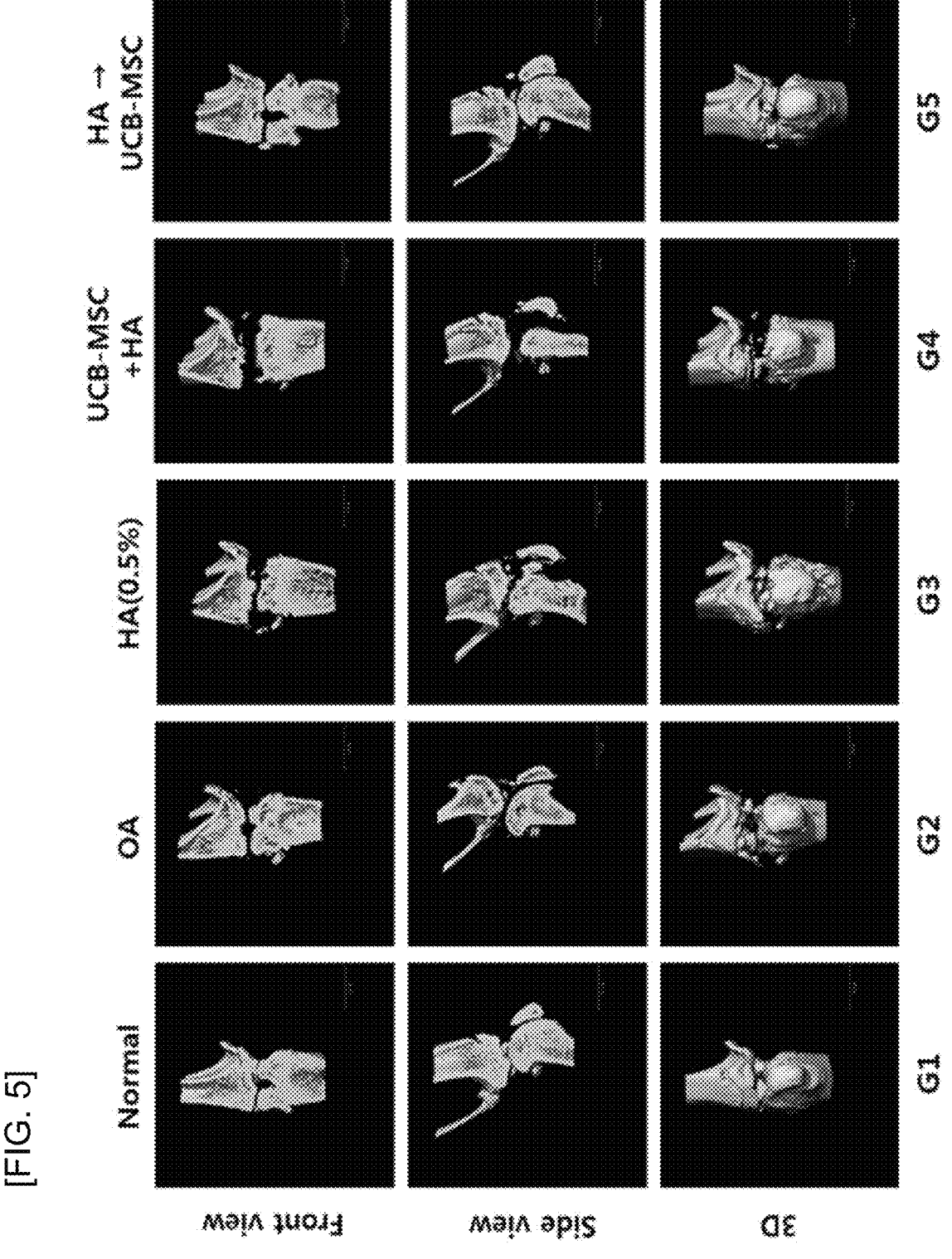

PHARMACEUTICAL COMPOSITION COMPRISING HYALURONIC ACID AND STEM CELLS FOR TREATING CARTILAGE DAMAGE-ASSOCIATED DISEASE

CROSS REFERENCE TO RELATED APPLICATIONS

This application is a National Stage of International Application No. PCT/KR2019/006816 filed Jun. 5, 2019, claiming priority based on U.S. Patent Application No. 62/680,748 filed Jun. 5, 2018.

TECHNICAL FIELD

The present invention relates to a pharmaceutical composition for treating a cartilage damage-associated disease, comprising hyaluronic acid and stem cells.

BACKGROUND ART

Degenerative arthritis is a disease in which due to gradual damage of and degenerative changes in the cartilage that protects the joint, the bones, ligaments, and the like which make up the joint are damaged to cause inflammation and pain. Hyaluronic acid (HA), which is used as one of drug therapy regimens for degenerative arthritis, is a component of the matrix in the joint cartilage and is a type of muco-polysaccharide involved in making proteoglycans. Currently, sodium hyaluronate (HYRURAN®) is being used to regenerate joint cartilage.

In addition, as researches on stem cells became active after the 2000s, a study has been conducted in which hyaluronic acid at a concentration of 0.5% is mixed with bone marrow or adipose-derived mesenchymal stem cells and administered to an osteoarthritis model (Alexander Mathiessen et al., *Arthritis Research & Therapy*, 19:18, 2017; Éva Kriston-Pál et al., *The Canadian Journal of Veterinary Research*, 81:73-78, 2017).

Furthermore, mesenchymal stem cells and hyaluronic acid are used in surgery in such a manner that the mesenchymal stem cells are mixed with hyaluronic acid of a concentration of 4% and the mixture is filled into a damaged cartilage area. However, intraarticular administration of sodium hyaluronate may be accompanied by adverse effects such as hypersensitivity reaction, temporary pain, swelling, and heat sensation (The Journal of the Korean Pain Society, 2004. 17. 170-174). In addition, hyaluronic acid of a concentration of 4% has a disadvantage in that such a concentration is relatively high and thus causes inconvenience for the hyaluronic acid to be used as an injection formulation.

Therefore, regarding treatment of arthritis using hyaluronic acid and stem cells, there is a need for continuous research on an optimized treatment method.

DISCLOSURE OF INVENTION

Technical Problem

The present inventors have conducted intensive studies to find a method for effectively treating a cartilage damage-related disease using hyaluronic acid and mesenchymal stem cells. As a result, the present inventors have identified that for osteoarthritis-induced rats, an excellent therapeutic effect on arthritis is observed in a case where hyaluronic acid is first administered followed by administration of mesenchymal stem cells, as compared with a case where hyaluronic acid and mesenchymal stem cells are administered in admixture; and thus have completed the present invention.

Solution to Problem

In an aspect of the present invention, there is provided a pharmaceutical composition for treating a cartilage damage-associated disease, comprising hyaluronic acid and mesenchymal stem cells, wherein when the pharmaceutical composition is administered to a patient in need thereof, the hyaluronic acid is first administered followed by administration of the mesenchymal stems.

In another aspect of the present invention, there is provided a method for treating a cartilage damage-associated disease, comprising steps of: (i) administering hyaluronic acid to an individual; and (ii) administering mesenchymal stem cells to the individual, after step (i).

Advantageous Effects of Invention

In a case where hyaluronic acid is first administered followed by administration of mesenchymal stem cells according to the present invention, the administration made in such a sequence can result in an excellent disease symptom-ameliorating effect in joint tissue affected by arthritis and can result in decreased weight bearing on knee, as compared with a case where hyaluronic acid and mesenchymal stem cells are administered in admixture. Therefore, the pharmaceutical composition of the present invention can be effectively used to treat a cartilage damage-associated disease.

BRIEF DESCRIPTION OF DRAWINGS

FIG. 1 illustrates photographs obtained by performing staining of joint tissue of rats in Groups G1 to G5 with hematoxylin and eosin (H & E), safranin-O, and anti-type II collagen antibodies.

FIG. 2 graphically illustrates results obtained by performing staining of joint tissue of rats in Groups G1 to G5, and then scoring the tissue depending on severity of lesion.

FIG. 3 illustrates a view in which weight bearing is measured in a rat using the Panlab Incapacitance tester.

FIG. 4 illustrates results obtained by measuring weight bearing in rats at week 0 and week 16.

FIG. 5 illustrates photographs, taken by Micro-CT, of joint tissue of rats in Groups G1 to G5.

BEST MODE FOR CARRYING OUT THE INVENTION

Hereinafter, the present invention will be described in detail.

In an aspect of the present invention, there is provided a pharmaceutical composition for treating a cartilage damage-associated disease, comprising hyaluronic acid and mesenchymal stem cells, wherein when the pharmaceutical composition is administered to a patient in need thereof, the hyaluronic acid is first administered followed by administration of the mesenchymal stem cells.

The hyaluronic acid is a linear polysaccharide polymer in which the monomers, N-acetylglucosamine and D-glucuronic acid, are repeatedly linked to each other. The hyaluronic acid is a biocompatible substance that helps heal wounds.

In addition, the hyaluronic acid is insoluble in aqueous solution through formation of ether bonds, and also has excellent viscoelasticity and high moisture absorption ability, which allows the hyaluronic acid to be decomposed and absorbed in a living body after maintaining its shape for a certain period of time in the body. However, natural hyaluronic acid is rapidly decomposed by hyaluronidase when injected into the body. Thus, to regulate such a decomposition rate, the natural hyaluronic acid may be crosslinked in various ways or may be made into a hyaluronic acid derivative by structural modification using a chemical substance such as benzyl alcohol, and then used.

The hyaluronic acid may be natural hyaluronic acid, a salt thereof, a derivative thereof, or a mixture thereof. The salt of hyaluronic acid may be in any salt form suitable for application to a living body, and examples thereof may include sodium hyaluronate, potassium hyaluronate, magnesium hyaluronate, zinc hyaluronate, cobalt hyaluronate, tetrabutylammonium hyaluronate, or any combination thereof. In addition, the derivative of hyaluronic acid may be a hyaluronic acid crosslinked product obtained by crosslinking natural hyaluronic acid or a salt thereof using a cross-linking agent.

The hyaluronic acid may be prepared into an injection formulation as a solution and used. The hyaluronic acid solution refers to a solution obtained by dissolving natural hyaluronic acid, a salt thereof, a mixture thereof, or a derivative thereof in physiological saline, phosphate buffered saline, or biocompatible saline. The hyaluronic acid solution may be prepared into an injection formulation such as an aqueous solution, a suspension, or an emulsion by addition of a diluent, a dispersant, a surfactant, a binder, and a lubricant, depending on a purpose of administration.

A concentration of hyaluronic acid in the hyaluronic acid solution may be 0.5% (w/v) to 2.0% (w/v), 0.7% (w/v) to 1.8% (w/v), 0.8% (w/v) to 1.6% (w/v), or 1.0% (w/v) to 1.5% (w/v). In a case where the hyaluronic acid solution is within the above-described concentration range, the hyaluronic acid solution may exhibit an excellent therapeutic effect and may have a viscosity suitable for being filled into a syringe or ampoule container so that the hyaluronic acid solution can be easily administered to an affected area of an individual. The hyaluronic acid may be administered intraarticularly. In an embodiment of the present invention, a hyaluronic acid solution at a concentration of 0.5% (w/v) was filled into a syringe and administered intraarticularly.

The mesenchymal stem cells may be mesenchymal stem cells obtained from various source. Specifically, the mesenchymal stem cells may be obtained from mammals including humans. In addition, the mesenchymal stem cells may be mesenchymal stem cells derived from tissues of various origins. Preferably, the mesenchymal stem cells may be derived from umbilical cord blood.

The mesenchymal stem cells may be prepared into an injection formulation as a separate solution from the hyaluronic acid solution and used. Specifically, the mesenchymal stem cell solution may be a solution obtained by suspending mesenchymal stem cells in physiological saline, phosphate buffered saline, biocompatible saline, or culture medium. In addition, the mesenchymal stem cell solution may be a solution in a state where after mesenchymal stem cells, which have been stored frozen, are thawed, a freezing solution thereof is contained as it is. The mesenchymal stem cell solution may be prepared into an injection formulation such as an aqueous solution, a suspension, or an emulsion by addition of a diluent, a dispersant, a surfactant, a binder, and a lubricant, depending on a purpose of administration.

The mesenchymal stem cells may be contained in an amount of $1\times10^5$ cells/ml to $1\times10^8$ cells/ml in the mesenchymal stem cell solution. Specifically, the mesenchymal stem cells may be contained in an amount of $1\times10^5$ cells/ml to $1\times10^8$ cells/ml, $2\times10^5$ cells/ml to $5\times10^7$ cells/ml, $5\times10^5$ cells/ml to $2\times10^7$ cells/ml, $1\times10^6$ cells/ml to $1\times10^7$ cells/ml, or $2\times10^6$ cells/ml to $5\times10^6$ cells/ml. In an embodiment of the present invention, a solution containing mesenchymal stem cells at $5\times10^4$ cells was filled into a syringe and administered intraarticularly.

The mesenchymal stem cells may be administered immediately after administration of the hyaluronic acid to an affected area of an individual, or the administration of mesenchymal stem cells may be made at an interval of 1 hour to 48 hours, 3 hours to 36 hours, 6 hours to 24 hours, or 9 hours to 12 hours.

The cartilage damage-associated disease refers to a disease that occurs due to damage, degeneration, loss, or defect of cartilage or cartilage tissue caused by mechanical stimuli or inflammatory responses. The cartilage damage-related disease may be a disease caused by damage, degeneration, loss, or defect of cartilage or cartilage tissue, or may be a disease caused by inflammation of surrounding synovial membrane or articular capsule without any damage, degeneration, loss, or defect of cartilage or cartilage tissue. Specifically, the cartilage damage-associated disease may include, but is not limited to, osteoarthritis, meniscus tear, arthrosis deformans, or chondromalacia.

A site where the osteoarthritis occurs may be jaw joint, shoulder joint, elbow joint, wrist joint, finger joint, spine joint, hip joint, knee joint, ankle joint, or toe joint. The pharmaceutical composition may be administered intraarticularly to the joint.

In another aspect of the present invention, there is provided a method for treating a cartilage damage-associated disease, comprising steps of: (i) administering hyaluronic acid to an individual; and (ii) administering mesenchymal stem cells to the individual, after step (i).

The hyaluronic acid and the mesenchymal stem cells are the same as described above in the pharmaceutical composition. In addition, the cartilage damage-associated disease is the same as described above in the pharmaceutical composition.

The individual may be an individual suffering from a cartilage damage-associated disease. In addition, the individual may be a mammal, specifically, a human.

A dose of the hyaluronic acid may be 0.5 mg/kg to 1.0 mg/kg. In an embodiment of the present invention, 25 μl of hyaluronic acid solution at a concentration of 10 mg/ml was administered to rats weighing 300 g to 350 g. Here, an amount of the hyaluronic acid administered to one rat is 0.25 mg, which corresponds to a dose of 0.7 mg/kg to 0.8 mg/kg in terms of kg body weight.

In addition, a dose of the mesenchymal stem cells may be $1\times10^6$ cells/individual to $1\times10^8$ cells/individual. The dose of the mesenchymal stem cells may be increased or decreased depending on size of cartilage damage area to be treated. Generally, for an adult knee joint having a size of about 2 cm², the mesenchymal stem cells at about $2\times10^6$ to $1\times10^8$ cells may be administered.

Specifically, the dose of the mesenchymal stem cells may be $5\times10^4$ cells/kg to $1\times10^6$ cells/kg, $1\times10^5$ cells/kg to $7\times10^5$ cells/kg, or $2\times10^5$ cells/kg to $5\times10^5$ cells/kg. In addition, the dose of the hyaluronic acid may be 0.5 mg/kg to 1.0 mg/kg, and the dose of the mesenchymal stem cells may be $1\times10^6$ cells/individual to $1\times10^8$ cells/individual.

The hyaluronic acid and the mesenchymal stem cells may be appropriately administered to an individual according to conventional methods, routes of administration, and dosages used in the art, if necessary. As an example of the route of administration, intraarticular administration may be mentioned. In addition, appropriate dosage and number of administrations may be selected according to methods known in the art, and amount of the composition to be actually administered and number of administrations may be appropriately determined by various factors such as type of symptoms to be prevented or treated, route of administration, sex, health condition, diet, individual's age and weight, and severity of disease.

MODE FOR THE INVENTION

Hereinafter, the present invention will be described in more detail by way of the following examples. However, the following examples are for illustrative purposes only, and the scope of the present invention is not limited thereto.

Example 1: Production of Osteoarthritis-Induced Rats and Drug Administration To produce osteoarthritis-induced rats, Sprague-Dawley rats were anesthetized by intraperitoneal administration of ZOLETIL™ 50 (VIRBAC, France) at a dose of 5 mg/kg and xylazine (ROMPUN®, Bayer AG, Germany) at a dose of 2.5 mg/kg. Then, the areas around the both knees were shaved using clipper. An area to be incised was disinfected with povidone and 70% alcohol, and then the knee skin was incised. The surrounding skin tissue was subjected to blunt dissection to expose an articular surface at the distal end of the right femur. Then, the anterior cruciate ligament was cut with scissors, and the wound was sutured using 4-0 nylon. After 7 days, monosodium iodoacetate (MIA), which causes cartilage destruction and pain, was filled into a 1-ml syringe, and administered intraarticularly in an amount of 50 μl at a concentration of 60 mg/ml. For the left knee, only administration of MIA was performed without cutting the anterior cruciate ligament.

The normal rat model and the osteoarthritis-induced rat model were used to make a total of 5 groups. The rats in each group were anesthetized by intraperitoneal administration of ZOLETIL™ 50 at a dose of 5 mg/kg and xylazine at a dose of 2.5 mg/kg. The right knee, which was an area for administration, was disinfected with povidone and 70% alcohol. Then, the joint cavity was identified with C-arm (ARCADIS™ Varic, SIEMENS AG), and the drugs were administered into the right knee joint cavity using an insulin syringe equipped with a 31-gauge needle. At week 16 after administration, histopathological examination and weight bearing test (incapacitance test) were performed.

Here, hyaluronic acid was prepared as a solution at a concentration of 10 mg/ml (0.5%) and administered each in an amount of 25 μl. In addition, mesenchymal stem cells at $5 \times 10^4$ cells were administered per rat. The mesenchymal stem cells (MEDIPOST, Korea) used were those obtained by thawing the mesenchymal stem cells that had been first isolated from umbilical cord blood and then stored frozen in liquid nitrogen.

In addition, Group G1 was a normal rat group to which no drugs had been administered, and Group G2 was an osteoarthritis-induced rat group to which no drugs had been administered. In addition, Group G3 was an osteoarthritis-induced rat group to which hyaluronic acid at a concentration of 0.5% (w/v) had been administered, and Group G4 was an osteoarthritis-induced rat group to which hyaluronic acid at a concentration of 0.5% (w/v) and umbilical cord blood-derived mesenchymal stem cells had been administered in admixture. Group G5 was an osteoarthritis-induced rat group to which hyaluronic acid at a concentration of 0.5% (w/v) had been first administered followed by administration of umbilical cord blood-derived mesenchymal stem cells.

Example 2: Histopathological Examination

The rats in each group were sacrificed at week 16, and joint tissues were collected. Then, the tissues were subjected to demineralization, trimming, dehydration, paraffin embedding, and microtome cutting, to prepare specimens for histopathological examination. Then, staining was performed using hematoxylin and eosin (H & E), safranin-O, and anti-type II collagen antibodies, and observation was performed using an optical microscope (OLYMPUS BX53™, OLYMPUS, Japan) (FIGS. 1 and 2).

In addition, histopathological examination was performed based on photographs, taken by the optical microscope, of the results obtained by performing staining. The histopathological examination was performed by evaluating changes observed in osteoarthritis, in which the changes were evaluated in terms of 7 items classified as follows: i) articular surface irregularity, ii) articular surface ulceration, iii) fibrillation of cartilage, iv) exposure of subchondral bone caused by cartilage loss, v) degeneration or necrosis, vi) reduction in cartilage staining, and vii) replacement of fibrocartilage. Severity of each lesion was evaluated in a total of 4 grades: 0 for no lesion, 1 for mild lesion, 2 for moderate lesion, and 3 for severe lesion. The evaluation results, which were obtained by calculating average values for the respective groups, are shown in Table 1 below.

TABLE 1

| n = 8 | G1 | G2 | G3 | G4 | G5 |
|---|---|---|---|---|---|
| Articular surface irregularity | 0.1 | 2.9 | 3 | 2.9 | 2.4 |
| Articular surface ulceration | 0 | 2.8 | 2.6 | 2.4 | 1.9 |
| Fibrillation of cartilage | 0 | 2.9 | 2.9 | 2.9 | 2.6 |
| Exposure of subchondral bone caused by cartilage loss | 0 | 2 | 1.6 | 1.6 | 1.4 |
| Degeneration | 0.9 | 3 | 3 | 2.7 | 2.6 |
| Reduction of cartilage staining | 0.9 | 2.8 | 2.3 | 2.4 | 2 |
| Replacement of fibrocartilage | 0 | 2.8 | 2.8 | 2.4 | 2.1 |

As shown in Table 1, Group G5 was significantly lower than Group G4 in terms of ulceration, cartilage degeneration, and reduction of cartilage staining. In addition, Group G5 showed a lower tendency than Group G4 even in terms of most of the rest items.

First, regarding i) articular surface irregularity, it was shown that Group G5 was lower than Group G4. It was observed that all arthritis-induced groups (G2 to G5) were significantly higher than Group G1 (p<0.001) in terms of articular surface irregularity.

In addition, regarding ii) articular surface ulceration, it was shown that Group G5 was significantly lower than Group G2 (p<0.05); and it was shown that Group G4 had 2.4, whereas Group G5 had 1.9 that was lower than Group G4. It was observed that all arthritis-induced groups (G2 to G5) were significantly higher than Group G1 (p<0.001) in terms of articular surface ulceration.

Furthermore, regarding iii) fibrillation of cartilage, it was shown that Group G4 had 2.9, whereas Group G5 had 2.6 that was lower than Group G4. It was shown that all arthritis-induced groups (G2 to G5) were significantly higher than Group G1 (p<0.001) in terms of fibrillation of cartilage.

In addition, regarding iv) exposure of subchondral bone, it was shown that Group G5 was lower than Group G4. It was shown that all arthritis-induced groups (G2 to G5) were significantly higher than Group G1 (p<0.001 or p<0.01) in terms of exposure of subchondral bone.

Furthermore, regarding v) degeneration, it was shown that Group G5 was lower than Group G4. It was shown that all arthritis-induced groups (G2 to G5) were significantly higher than Group G1 (p<0.001 or p<0.01) in terms of degeneration.

In addition, regarding vi) reduction of cartilage staining, it was shown that Group G5 was lower than Group G4. It was shown that all arthritis-induced groups (G2 to G5) were significantly higher than Group G1 (p<0.001 or p<0.01) in terms of reduction of cartilage staining.

Furthermore, regarding vii) replacement of fibrocartilage, it was shown that Group G5 was lower than Group G4. It was shown that all arthritis-induced groups (G2 to G5) were significantly higher than Group G1 (p<0.001 or p<0.01) in terms of replacement of fibrocartilage.

Example 3: Weight Bearing Test

A weight bearing test was performed using Panlab Incapacitance tester by causing a plastic fixture for rats to be erected at an inclination of 60 degrees at week 0 and week 16 after drug administration, and then calculating an average of force that had been applied for 10 seconds to hindlimbs of rats in each group. A percentage of body weight distributed in the hindlimbs injected with the drugs was measured through the following calculation expression (FIG. 3).

[Calculation Expression 1]

$$\text{Percentage (\%)} = \frac{\text{Induced hindlimb weight}}{\text{Normal hindlimb weight}} \times 100$$

As a result, at week 16 after drug administration, it was shown that all arthritis-induced groups (G2 to G5) were statistically significantly lower than Group G1 (p<0.001) in terms of weight bearing. In addition, Group G4 had significantly improved weight bearing as compared with Group G3 (p<0.05). Furthermore, Group G5 had significantly improved weight bearing as compared with Groups G3 and G4 (p<0.05 and p<0.001). From these results, it was identified that in a case where hyaluronic acid was first administered followed by administration of mesenchymal stem cells, the administration made in such a sequence could relieve pain caused by weight bearing (FIG. 4).

Example 4: Micro-Computed Tomography (Micro-CT)

Photographs of damaged areas in knee joint were taken by Micro-CT before drug administration and after sacrifice at week 16. Evaluation of knee joint was performed by analyzing, with a program (HP DECWINDOWS™ Motif for OpenVMS, Version 1.7), structural elements and bone density in transverse cross-sectional images of the tibia and the femur.

First, the analysis results for the tibia, which were obtained by calculating average values for the respective groups, are shown in Table 2 below.

TABLE 2

| Item | G1 (n = 8) | G2 (n = 8) | G3 (n = 8) | G4 (n = 8) | G5 (n = 8) |
|---|---|---|---|---|---|
| Bone volume/ total volume | 0.31 | 0.18 | 0.20 | 0.21 | 0.24 |
| Bone surface area/ bone volume | 3.24 | 4.17 | 3.78 | 4.01 | 3.71 |
| Bone trabecular number | 0.57 | 2.9 | 0.3 | 0.31 | 0.36 |
| Bone trabecular thickness | 0.52 | 0.32 | 0.38 | 0.38 | 0.37 |
| Bone trabecular separation | 1.16 | 2.52 | 2.08 | 2.16 | 1.94 |

As shown in Table 2, at week 16 after drug administration, Group G5 had significantly higher bone volume/total volume than Groups G2 and G4 (p<0.01). In addition, Group G5 had lower bone surface area/bone volume than Group G4.

Furthermore, it was found that at week 16, Group G5 had a tendency in which a significant difference or improvement was observed as compared with Group G4 in terms of both bone trabecular number and bone trabecular separation, except bone trabecular thickness.

In addition, the analysis results for the femur, which were obtained by calculating average values for the respective groups, are shown in Table 3 below.

TABLE 3

| Item | G1 (n = 8) | G2 (n = 8) | G3 (n = 8) | G4 (n = 8) | G5 (n = 8) |
|---|---|---|---|---|---|
| Bone volume/ total volume | 0.29 | 0.15 | 0.14 | 0.18 | 0.23 |
| Bone surface area/ bone volume | 3.49 | 4.30 | 3.77 | 4.24 | 3.74 |
| Bone trabecular number | 0.56 | 0.28 | 0.28 | 0.30 | 0.39 |
| Bone trabecular thickness | 0.55 | 0.39 | 0.43 | 0.47 | 0.37 |
| Bone trabecular separation | 1.23 | 2.73 | 2.81 | 2.53 | 2.11 |

As shown in Table 3, at week 16 after drug administration, Group G5 had significantly higher bone volume/total volume than Group G2 (p<0.01) and also had higher bone volume/total volume than Group G4. In addition, it was shown that Group G5 had lower bone surface area/bone volume than Group G4, and Group G5 had higher bone trabecular number than Group G4. It was shown that Group G5 had significantly lower bone trabecular separation than Group G2 (p<0.05) and also had lower bone trabecular separation than Group G4.

Furthermore, it was identified that at week 16, Group G5 had a tendency in which a significant difference or improvement was observed as compared with Group G4 in terms of all test items except bone trabecular thickness (FIG. 5).

The invention claimed is:

1. A method for treating a subject with a cartilage damage-associated disease, comprising steps of:

(i) administering a first composition that is a hyaluronic acid solution consisting of hyaluronic acid, a salt thereof, or a derivative thereof, dissolved in a physiological saline, phosphate buffered saline, or a biocompatible saline, to the subject; and (ii) administering a second composition comprising mesenchymal stem cells to the subject, at an interval of 1 hour to 48 hours after step (i), thereby treating the cartilage damage-associated disease, wherein the mesenchymal stem cells of step (ii) are derived from umbilical cord blood, wherein the hyaluronic acid solution of step (i) has a concentration of 0.5% (w/v) to 1% (w/v) of hyaluronic acid, a salt thereof, or a derivative thereof, wherein the administration of the first and second compositions increases bone trabecular number and decreases bone trabecular separation in the subject, wherein the first composition is an injection formulation of hyaluronic acid solution, and wherein the second composition of step (ii) is an injection formulation of mesenchymal stem cell solution, is free from hyaluronic acid, prepared as a separate formulation from the hyaluronic acid solution by suspending mesenchymal stem cells in physiological saline, phosphate buffered saline, biocompatible saline, or culture medium.

2. The method of claim 1, wherein the mesenchymal stem cells are contained in an amount of $1.0 \times 10^5$ cells/ml to $1.0 \times 10^8$ cells/ml of the second composition.

3. The method of claim 1, wherein the first composition is administered at a dose of 0.5 to 1.0 mg/kg, body weight and the second composition is administered at a dose of $5 \times 10^4$ cells/kg to $1 \times 10^6$ cells/kg body weight.

4. The method of claim 1, wherein the cartilage damage-associated disease is osteoarthritis, meniscus tear, arthrosis deformans, or chondromalacia.

5. The method of claim 1, wherein a site of the subject where the osteoarthritis occurs is jaw joint, shoulder joint, elbow joint, wrist joint, finger joint, spine joint, hip joint, knee joint, ankle joint, or toe joint.

6. The method of claim 5, wherein the first composition is administered to the site at a dose of 0.5 to 1.0 mg/kg body weight, and the second composition is administered at a dose of $2 \times 10^6$ cells to $1 \times 10^8$ cells.

7. The method of claim 1, wherein the first and the second compositions are administered intraarticularly.

8. The method of claim 1, wherein the interval is 3 hours to 36 hours.

9. The method of claim 1, wherein the interval is 6 hours to 24 hours.

10. The method of claim 1, wherein the interval is 9 hours to 12 hours.

* * * * *